(12) United States Patent
Kobayashi et al.

(10) Patent No.: US 6,417,368 B1
(45) Date of Patent: Jul. 9, 2002

(54) AMINE DERIVATIVE FIXED TO RESIN AND METHOD FOR SYNTHESIZING β-AMINOCARBONYL COMPOUND IN A SOLID PHASE

(75) Inventors: Shu Kobayashi; Yoji Aoki, both of Tokyo (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/646,042

(22) PCT Filed: Mar. 12, 1999

(86) PCT No.: PCT/JP99/01221

§ 371 (c)(1),
(2), (4) Date: Nov. 8, 2000

(87) PCT Pub. No.: WO99/46239

PCT Pub. Date: Sep. 16, 1999

(30) Foreign Application Priority Data

Mar. 13, 1998 (JP) .............................. 10-082777

(51) Int. Cl.[7] ..................... C07C 251/24; C07C 217/58; C07C 229/34; C07D 213/74; C07F 7/18
(52) U.S. Cl. ..................... 546/335; 558/252; 558/256; 560/38; 560/39; 560/40; 560/42
(58) Field of Search ..................... 546/335; 558/252, 558/256; 560/38, 39, 40, 42

(56) References Cited

PUBLICATIONS

Kobayashi et al. 'Activation of imines by rare earth metal triflates. Ln(OTf)3 or Sc(OTf)3 catalyzed reactions of imines with silyl enolates and Diels–Alder reactions of imines.' Synlett 1995 pp. 233–234.*

* cited by examiner

*Primary Examiner*—Brian J. Davis
(74) *Attorney, Agent, or Firm*—Wenderoth, Lind & Ponack, LLP

(57) ABSTRACT

The invention provides a resin-immobilized imine represented by the following formula:

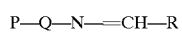

P—Q—N═CH—R    I

[in the formula, P represents the principal chain of a resin polymer; Q represents a substituted or unsubstituted hydrocarbon side chain or a substituted or unsubstituted hydrocarbon side chain with a heteroatom interposed therein; R represents a substituted or unsubstituted hydrocarbon group or heterocyclic group] and a resin-immobilized β-aminocarbonyl compound of the following formula:

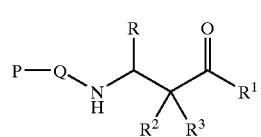

II which can be released as β-aminocarbonyl compound from the solid phase; and the invention also provide a resin-immobilized amine of the following formula:

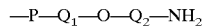

—P—Q$_1$—O—Q$_2$—NH$_2$    III

[Q$_1$ and Q$_2$ independently represent a hydrocarbon chain such as arylene, alkylenearylene or arylenealkylene], which is essential for solid state synthesis; and the invention has enabled the solid state synthesis of β-aminocarbonyl compound by the application of iminoaldol reaction.

6 Claims, No Drawings

AMINE DERIVATIVE FIXED TO RESIN AND METHOD FOR SYNTHESIZING β-AMINOCARBONYL COMPOUND IN A SOLID PHASE

This application is a 371 of PCT/JP99/0122, filed Mar. 12, 1999.

BACKGROUND OF THE INVENTION

1. Field of the Invention

The present invention relates to a resin-immobilized amine derivative and a solid state synthesis method of β-aminocarbonyl compound.

2. Description of the Related Art

For peptide synthesis, for example, solid state synthesis methods using resin carriers have been known conventionally. Such solid state synthesis methods are effective means for simultaneous synthesis of a group of numerous types of analogous compounds. It has been suggested that solid state synthesis methods are applicable to various chemical reactions.

Practically, however, reactions to which solid state reaction is applicable are limited, disadvantageously, compared with liquid phase reaction as the principal reaction for chemical synthesis.

In such circumstances of the related art concerning solid state synthesis methods, the inventors of the present application have investigated about the enhancement of the effectiveness of solid state synthesis methods by efficiently progressing the most essential and important reaction for generating carbon—carbon bond in organic synthesis in solid phase.

The inventors of the application have found a new method for iminoaldol-type addition reaction with a catalyst, using as the starting material an imine compound recovered from the reaction of an amine compound with aldehydes. Therefore, it has increasingly been an important problem to establish a solid state synthesis method capable of practically more enhancing the efficiency of the method.

It is therefore a purpose of the invention of the application to provide new technical means for realizing the iminoaldol-type addition reaction as described above by a solid state synthesis method; more specifically, it is a purpose of the invention to provide a method for synthesizing β-aminocarbonyl compounds, comprising applying a solid state synthesis reaction.

SUMMARY OF THE INVENTION

So as to attain the foregoing objectives, the present application provides a resin-immobilized β-aminocarbonyl compound represented by the following formula in a first aspect of the invention:

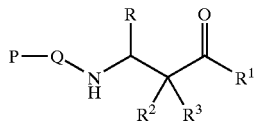

wherein P represents the principal chain of a resin polymer; Q represents a substituted or unsubstituted hydrocarbon side chain or a substituted or unsubstituted hydrocarbon side chain with a heteroatom interposed therein; R, and $R^2$ and $R^3$ independently represent a substituted or unsubstituted hydrocarbon group or heterocyclic group; $R^1$ represents $—OR^0$, $—SR^0$ or $R^0$ ($R^0$ represents a substituted or unsubstituted hydrocarbon group or heterocyclic group).

In a second aspect of the invention, the application provides a resin-immobilized β-aminocarbonyl compound of the aforementioned formula where, the hydrocarbon side chain Q represents the following formula:

$—Q_1—O—Q_2—$ (in formula, $Q_1$ and $Q_2$ independently represent a substituted or unsubstituted hydrocarbon chain such as arylene, alkylenearylene or arylenealkylene).

The application provides a method for producing a resin-immobilized β-aminocarbonyl compound in a third aspect of the invention, comprising allowing a resin immobilized imine of the formula I: P—Q—N═CH—R to react with a silyl ether.

In a fourth aspect of the invention, the application provides a method for producting β-aminocarbonyl compound represented by either one of the following formulas (A)

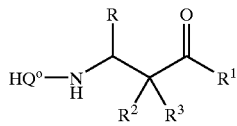

(where $Q^0$ represents a substituent which is the remaining part of the side chain Q after the β-aminocarbonyl compound is separated from the resin) or (B)

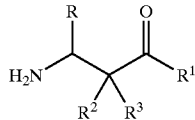

comprising the cleavage of the β-aminocarbonyl from the resin of the resin-immobilized β-aminocarbonyl compound.

In a fifth aspect of the invention, the application provides a method for producing a β-aminocarbonyl compound, comprising treatment of the resin-immobilized β-aminocarbonyl compound of above formula II with a Lewis acid.

DETAILED DESCRIPTION OF THE INVENTION

The application provides a resin-immobilized β-aminocarbonyl compound represented by the formula II according to the first and second aspects of the invention. These have never been know to enable the solid state synthesis method of β-aminocarbonyl compounds.

In the resin-immobilized β-aminocarbonyl compound of the formula II, as described above, P represents the principal chain of a resin polymer and Q represents a side chain to bind to the principal chain, wherein the resin polymer composing the principal chain includes any of addition polymers, condensed polymers and cross-linked polymers thereof but preferably includes addition polymers of alkenes with carbon—carbon double bond or cross-linked polymers thereof. The alkenes include aliphatic olefins and aliphatic dienes and also include, α, β-aliphatic unsaturated carboxylic acids or esters thereof, α, β-aliphatic unsaturated nitriles and aromatic alkenes such as styrene, α-methylstyrene and divinylbenzene. The addition polymers thereof or partially cross-linked polymers thereof are preferable.

It is needless to say that various condensed polymers of polyester, epoxy resins, polyether and polyamide are also included.

In accordance with the invention, the side chain Q includes substituted or unsubstituted hydrocaron chains or substituted or unsubstituted hydrocarbon chains with heteroatoms such as oxygen atom or nitrogen atom interposed therein, wherein the hydrocarbon chains then include various hydrocarbon chains such as aliphatic, alicyclic, aromatic and aromatic aliphatic hydrocarbon chains and are for example alkylene chain represented by —$(CH_2)_n$— and phenylenealkylene chain. Otherwise, the hydrocarbon chains can satisfactorily be hydrocarbon chains with heteroatoms interposed therein.

These side chains Q are satisfactorily formed together with the principal chain P and are also satisfactorily formed by graft polymerization after the principal chain P is formed.

As the side chain Q, for example, hydrocarbon chains derived from the resin-immobilized amine P—$Q_1$—O—$Q_2$—$NH_2$ are provided in accordance with the invention, wherein $Q_1$ and $Q_2$ are arylene, alkylenearylene or arylenealkylene. Specifically, preferable examples of the hydrocarbon chains are hydrocarbon chains with Ph (pheylene chain), such as —Ph—, —$(CH_2)_n$—Ph, —PH—$(CH_2)_n$—, —Ph—$(CH_2)_n$—Ph—, particularly oxyphenylene chains, such as —Ph—O—Ph—, —Ph—$(CH_2)_n$—O—Ph—, —Ph—$(CH_2)_n$—O—$(CH_2)_n$—Ph.

These hydrocarbons can satisfactorily have various substituents with no inhibition of the solid state synthesis reaction but with an activity to activate the reaction. The substituents include hydrocarbon groups such as alkyl group and aryl group, halogen atom, alkoxyl group, acyloxy group, alkoxycarbonyl group, nitro group, cyano group and heterocyclic group.

R, $R^2$ and $R^3$, and $R^0$ composing $R^1$ in the resin-immobilized β-aminocarbonyl group of the formula II represent substituted or unsubstituted hydrocarbon groups or heterocyclic groups, wherein the hydrocabon groups include various linear or cyclic aliphatic or aromatic or aromatic aliphatic hydrocarbon groups, saturated or unsaturated. Similary, the heterocyclic groups include various heterocyclic groups containing oxygen or nitrogen. These are satisfactorily substituted with various substituents with no inhibition of the solid state synthesis reaction but with an activity to activate the reaction, for example hydrocarbon groups such as alkyl group and aryl group, halogen atom, alkoxyl group, acyloxy group, alkoxycarbonyl group, nitro group, cyano group and heterocyclic group.

In accordance with the invention, further, the resin-immoiblized amine of the formula III P—$Q_1$—O—$Q_2$—$NH_2$ is provided as a substrate for the solid state synthesis of compounds containing nitrogen such as amino group. The resin-immobilized amine is essentially required for constructing a library of nitrogen-containing compounds for the solid state synthesis.

For example, —$Q_1$—O—$Q_2$— is more specifically described as such a structure as —Ph—$CH_2$—O—Ph—$CH_2$—.

The reaction of various resin-immobilized amines including the resin-immobilized amine with aldehydes generates the resin-immobilized amine (imine?) of the formula I.

The resin-immobilized amine of the formula P—Q—$NH_2$ or P—$Q_1$—O—$Q_2$-$NH_2$, as produced by aminating for example a resin polymer of a structure P—QH and P—QX (in the formula, X represents halogen atom) or reducing an amide of the formula P—$Q_1$—O—$Q_2$—$CONH_2$ (in the formula, $Q_1$ represents a part of the side chain Q), is allowed to react with aldehydes.

The resin-immobilized imine synthesis through the reaction with aldehydes is appropriately carried out in a solvent at a temperature of about −10 to 70° C., preferably about 10 to 60° C. The solvent appropriately includes DMF, DMSO, nitriles and halogenated hydrocarbons.

During the reaction, aldehydes are appropriately used at an equivalent weight ratio to the resin-immobilized imine within a range of 1 to 10 during the reaction.

The resin-immobilized imine represented by the formula I can be used as a substrate for solid-phase iminoaldol reaction. The reaction is carried out by allowing the resin-immobilized imine of the formula I to react with the silyl ethers.

The solid state reaction with the silyl ethers is progressed in a solvent, using for example a rare earth Lewis acid catalyst. As the solvent, for example, use can be made of halogenated hydrocarbons, aromatic hydrocarbons, ethers, nitriles, alcohols and water or appropriate mixture solvents thereof.

The rare earth Lewis acid satisfactorily includes rare earth metal compounds with Lewis acidity, for example organic acid ester salts, alcoholates, organic metal compounds and organic complex compounds of rare earth elements such as ytterbium (Yb), scandium (Sc), yttrium (Y), lanthanoid (La), samarium (Sm) and neodium (Nd). Among them, rare earth triflate for example Yb(OTf)$_3$ is more appropriate.

The silyl ethers are used at an equivalent weight ratio of generally 0.5 to 10, preferably 1 to 7 to the resin-immobilized imine. The rare earth Lewis acid actalyst is used at an equivalent weight ratio of generally 0.01 to 1, preferably about 0.1 to 0.6.

The reaction temperature is appropriately −20 to 60° C., more preferably ambient temperature or therearound.

In accordance with the invention, the resin-immobilized β-aminocarbonyl compound can be recovered by the solid state reaction.

Together with the amine and imine, the resin-immobilized β-aminocarbonyl compound serves as important means for constructing a library of various nitrogen-containing organic compounds.

By cleavage of the β-aminocarbonyl compound from the immobilizing resin, the β-aminocarbonyl compound of either one of the formulas A and B can be recovered.

As shown in the following examples, for example, the selectivity to the formula A or B depends on the conditions for the cleavage reaction.

Lewis acid is effectively used for the cleavage reaction. By using Lewis acid, the β-aminocarbonyl compound can be detached under mild conditions in a smooth manner. Oxidative cleavage is also effective.

DESCRIPTION OF THE PREFERRED EMBODIMENTS

The invention will now be described in more detail in the following examples.

EXAMPLE 1

According to the following reaction scheme, chloromethylated polystyrene 1 reacted with p-hydroxybenzamide in the presence of sodium hydroxide, followed by reduction with borane, to recover resin-immobilized amine

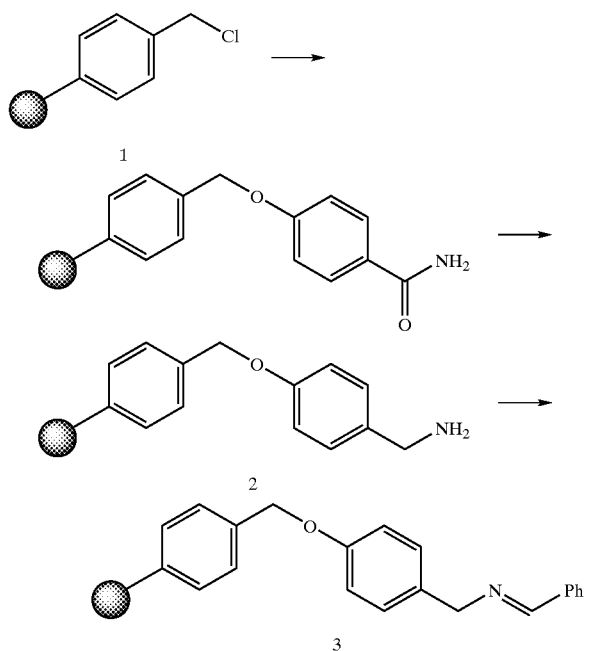

Benzaldehyde reacted with the resulting resin-immobilized amine 2, to recover the corresponding resin-immobilized imine 3.

According to the following reaction scheme, the resin-immobilized amine 3 reacted with silyl ether in the presence of a rare earth Lewis acid catalyst Yb (OTf)$_3$ of 20 mol % in a solvent dichloromethane at ambient temperature:

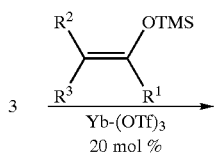

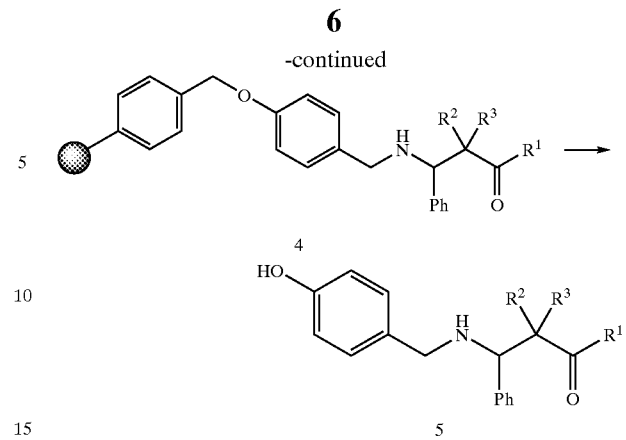

[in the formula, TMS represents trimethylsilyl group]. The resulting resin-immobilized β-aminocarbonyl compound 4 was subjected to a release process from the solid phase by using Lewis acid, to recover β-amino ester as β-aminocarbonyl compound 5, wherein the hydroxybenzyl group is bonded to the amino group.

The silyl ether type and release conditions were modified. The results are shown below in Table 1.

TABLE 1

| | | Conditions | Yield (%) |
|---|---|---|---|
| $R^2$, $R^3$, $R^1$ OTMS | | | |
| OTMS, OMe | 11 | TFA, 60° C., 3 h | 73 |
| | 11 | TFMSA, rt, 3 h | 63 |
| | 11 | TMSOTf (10 eq), CH$_2$Cl$_2$, rt, 3 h | 82 |
| BnO, O'Pr, OTMS | 12 | TMSOTf (10 eq), CH$_2$Cl$_2$, rt, 3 h | 78 |

The physico-chemical properties are shown below.
R═Ph, R$^2$, R$^3$═Me, R$^1$═OMe

TABLE 2

| | |
|---|---|
| $^1$H | 1. 03 (3 H, s), 1. 11 (3 H, s), 3. 32 (1 H, d, 13. 2 Hz), 3. 57 (1 H, d, 13. 2 Hz), 3. 65 (3 H, s), 3. 88 (1 H, s), 6. 74 (2 H, d, 8. 6 Hz), 7. 06 (2 H, d, 8. 6 Hz), 7. 25– 7. 36 (5 H, m) |
| $^{13}$C | 19. 5. 24. 2, 47. 6, 50. 9, 52 0. 67, 7, 115. 1, 127. 5, 128. 0, 129. 1. 129. 7, 132. 4, 139. 1, 154. 8, 178. 2 |
| IR | 3397, 1734 cm$^{-1}$ |

EXAMPLE 2

The same procedures as in Example 1 were carried out, except for the use of the rare earth Lewis acid catalyst at 30 mol % for reaction of various resin-immobilized imines with silyl ether and except that the resulting product was released from the solid phase by using a Lewis acid TMSOTf.

The results are shown in Table 3.

TABLE 3

| R | R² / R³ / R¹ (OTMS reagent) | | Yield (%) |
|---|---|---|---|
| Ph | OTMS, SEt (ketene silyl acetal) | | 52 |
| p-Cl-Ph | OTMS, OMe, with Me₂ | 11 | 58 |
| (4-methylphenyl) | | 11 | 95 |
| (2-pyridyl-methyl) | | 11 | 53 |
| C₈H₁₁ | | 11 | 60 |
| 2-Phenylethy | | 11 | 56 |

The physico-chemical properties are shown below.

R=Ph, R², R⁰=H, R¹=SE t

TABLE 4

| | |
|---|---|
| ¹H | 1. 21 (3 H, t, 7. 5 Hz), 2. 81–2. 99 (4 H, m), 3. 45 (1 H, d, 11. 7 Hz), 3. 55 (1 H, d, 11. 7 Hz), 4. 15 (1H, dd, 5. 0, 8. 6 Hz), 6 73 (2 H, d, 8. 4 Hz), 7. 10 (2 H, d, 8. 4 Hz), 7. 19–7. 40 (5 H, m), |
| ¹³C | 12. 3, 21. 4, 47, 8, 51. 3, 58. 9, 115. 6, 127. 3, 128. 2. 128. 7, 130. 2. 131. 4, 141. 2, 198. 2 |

R = Ph—Cl,
R³ = Me,
R¹ = OMe

TABLE 5

| | |
|---|---|
| ¹H | 1. 02 (3 H, s), 1. 09 (3 H, s), 3. 29 (1 H, d, 13. 2 Hz), 3. 55 (1 H, d, 13. 2 Hz), 3. 64 (3 H, s), 3. 84 (1 H, s), 6. 75 (2 H, d, 8. 6 Hz) 7. 05 (2 H, d, 8. 6 Hz), 7. 20 (2 H, d, 8. 4 Hz), 7. 31 (2 H, d, 8. 4 Hz) |
| ¹³C | 19. 5, 24. 0, 31. 0, 47. 3, 50. 7. 51. 9. 66. 9, 115. 0, 128. 1, 129. 5, 130. 4, 132. 2, 133. 1, 137. 6, 154. 6, 177. 6 |

R = 2-pyridyl,
R²,
R³ = Me,
R¹ = Ome

TABLE 6

| $^1H$ | 1. 06 (3 H, s) 1. 14 (3 H, s), 3. 30 (1 H, d, J = 13. 2 Hz), 3. 57 (1 H, d, J = 13. 2 Hz), 3. 64 (3 H, s), 3. 96 (1 H, s), 6. 70 (2 H, d, J = 8. 6 Hz), 7. 05 (2 H, d, J = 8. 6 Hz), 7. 20 (2 H, m), 7. 64 (1 H, t, 7. 7 Hz), 8. 60 (1 H, d, J = 4. 2 Hz) |
|---|---|
| $^{10}C$ | 19. 9, 23. 5, 47. 6, 51. 4, 51. 8, 67. 7, 115. 0, 122. 3. 124. 6, 129. 6, 135. 7, 149, 0, 154. 8, 177. 6 |

R = cyclohexyl,
$R^2$,
$R^3$ = Me,
$R^1$ = OMe

TABLE 7

| $^1H$ | 1. 14 (3 H, s), 1. 18 (3 H, s), 1. 25–1. 65 (10 H, m), 2. 09 (1 H, m), 2. 66 (1 H, m), 3. 64 (3 H, s), 3. 73 (1 H, d, 12. 6 Hz), 3. 88 (1 H, d, 12. 6 Hz), 6. 76 (2 H, d, 8. 4 Hz), 7. 18 (2 H, d, 8. 4 Hz) |
|---|---|

R = phenyletheyl,
$R^2$,
$R^3$ = Me,
$R^1$ = OMe

TABLE 8

| $^1H$ | 1. 08 (3 H, s), 1. 15 (3 H, s), 1. 55 (2 H, m, 2. 48–2. 60 (2 H, m), 3. 63 (3 H, s) 3. 71 (1 H, 12. 3 Hz), 3. 84 (1 H, d, 12. 3 Hz), 6. 70–6. 74 (3 H, m), 7. 10–7. 28 (6 H, m) |
|---|---|
| $^{13}C$ | 21. 4, 21. 8, 29. 7. 32. 8, 47. 7, 51. 8, 54. 0, 63. 3, 115. 3, 126. 0, 126. 5, 128. 3, 128. 4, 129. 4, 132. 1. 165. 9, 175. 1 |

IR 3337, 1732

EXAMPLE 3

The same procedures as in Example 2 were carried out except for the use of DDQ for releasing the product from the solid phase. The results are shown in Table 9.

TABLE 9

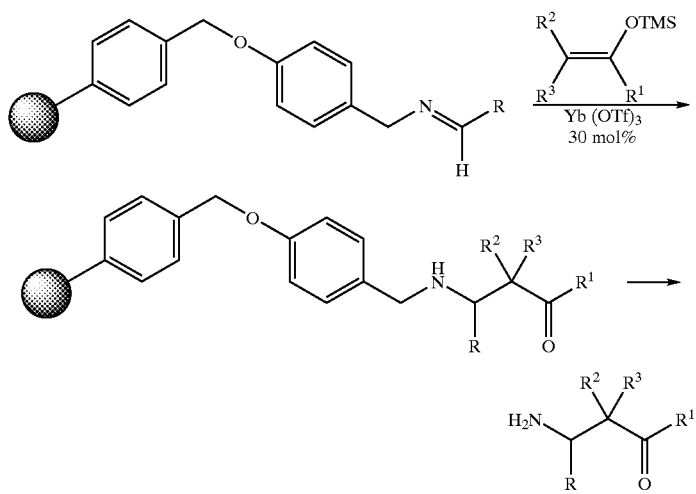

| R | $R^2$ $R^3$ $R^1$ (OTMS) | | Yield (%) |
|---|---|---|---|
| Ph | | 11 | 64 |
| Ph | | 12 | 53 |
| $C_8H_{11}$ | | 11 | 61 |

The physico-chemical properties are shown below.

R=Ph, $R^2$, $R^3$=Me, $R^1$=OMe

TABLE 10

| $^1H$ | 1. 09 (3 H, s), 1. 15 (3 H, s), 3. 70 (3 H, s), 4. 24 (1 H, s), 7. 28–7, 35 (5 H, m) |
|---|---|
| $^{13}C$ | 20. 6, 24. 2, 52. 0, 55. 7, 64. 5, 127, 4, 127. 8, 127. 9, 128. 3, 176. 9 |

R = cyclohexyl,
$R^2$,
$R^3$ = Me,
$R^1$ = OMe

TABLE 11

| $^1$H | 0.99 (3 H, s), 1.22 (3 H, s), 1.46–1.76 (10 H, m), 1.96 (1 H, m), 2.84 (1 H, d, 6.2 Hz), 3.64 (3 H, s) |
|---|---|
| $^{13}$C | 19.5, 22.9, 25.4, 25.7, 26.9. 26.2, 48.4, 54.5, 62.0 |

INDUSTRIAL APPLICABILITY

As has been described above in detail, the solid state synthesis of β-aminocarbonyl compound through the application of iminoaldol reaction is attained in accordance with the invention of the application; and additionally, a library of β-aminocarbonyl compounds can efficiently be constructed.

What is claimed is:

1. A resin-immobilized β-aminocarbonyl compound represented by the following formula:

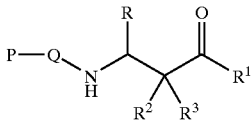

II wherein, P represents the principal chain of a resin polymer; Q represents a substituted or unsubstituted hydrocarbon side chain or a substituted or unsubstituted hydrocarbon side chain with a heteroatom interposed therein; R and $R^2$ and $R^3$ independently represent a substituted or unsubstituted hydrocarbon group or heterocyclic group; $R^1$ represents —$OR^0$, $SR^0$ or $R^0$ where $R^0$ represents a substituted or unsubstituted hydrocarbon group or heterocyclic group.

2. The resin-immobilized β-aminocarbonyl compound according to claim 1 wherein the hydrocarbon side chain Q represents the following formula:

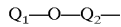

where, $Q_1$ and $Q_2$ independently represent a substituted or unsubstituted hydrocarbon chain.

3. The resin-immobilized β-aminocarbonyl compound according to claim 2 wherein $Q_1$ and $Q_2$ independently represent arylene, alkylenearylene or arylenealkylene.

4. A method for producing a resin immobilized β-aminocarbonyl compound according to claim 1 or 2 comprising allowing a resin-immobilized imine of the formula I: P—Q—N=CH—R to react with a silyl ether.

5. A method for producing a β-aminocarbonyl compound represented by at least one of the following formulas (A)

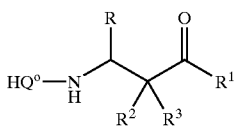

A where $Q^0$ represents a substituent which is the remaining part of the side chain Q after the β-aminocarbonyl compound is separated from the resin

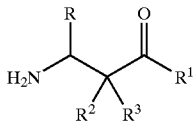

B which comprises cleavage of the β-aminocarbonyl from the resin of the resin-immobilized β-aminocabonyl compound of claim 1 or 2.

6. A method for producing a β-aminocarbonyl compound which comprises treatment of the β-aminocarbonyl compound of claim 1 or 2 with a Lewis acid.

* * * * *